US012661268B2

(12) United States Patent
Guse et al.

(10) Patent No.: US 12,661,268 B2
(45) Date of Patent: Jun. 23, 2026

(54) WELDING-TYPE HEADWEAR WITH ENHANCED MOVEMENT AND SOFT CLOSE

(71) Applicant: Illinois Tool Works Inc., Glenview, IL (US)

(72) Inventors: Matthew Guse, Oshkosh, WI (US); Kathryn Kleman, Oshkosh, WI (US); Lindsey Oldencamp, Kaukauna, WI (US); Jordan Kopac, III, De Pere, WI (US)

(73) Assignee: ILLINOIS TOOL WORKS INC., Glenview, IL (US)

( * ) Notice: Subject to any disclaimer, the term of this patent is extended or adjusted under 35 U.S.C. 154(b) by 0 days.

(21) Appl. No.: 18/968,436

(22) Filed: Dec. 4, 2024

(65) Prior Publication Data

US 2025/0221859 A1     Jul. 10, 2025

Related U.S. Application Data

(60) Provisional application No. 63/619,040, filed on Jan. 9, 2024.

(51) Int. Cl.
    *A61F 9/06*     (2006.01)
    *A42B 3/22*     (2006.01)
(52) U.S. Cl.
    CPC .............. *A61F 9/061* (2013.01); *A42B 3/223* (2013.01); *A42B 3/225* (2013.01)
(58) Field of Classification Search
    CPC . A61F 9/06; A61F 9/061; A42B 3/221; A42B 3/222; A42B 3/223; A42B 3/225
    See application file for complete search history.

(56) References Cited

U.S. PATENT DOCUMENTS

| | | | | |
|---|---|---|---|---|
| 4,185,328 A | * | 1/1980 | Graveno | .................. A61F 9/06 2/8.1 |
| 4,422,185 A | | 12/1983 | Cook | |
| 4,748,696 A | | 6/1988 | Fohl | |
| 4,853,973 A | | 8/1989 | Boochard | |
| 11,832,676 B2 | * | 12/2023 | Nassimi | .................. A42B 3/24 |

(Continued)

FOREIGN PATENT DOCUMENTS

DE     102009051780     1/2011

OTHER PUBLICATIONS

Extended European Search Report for Appln No. 25150037.7, dated Jun. 6, 2025, 8 pages.

*Primary Examiner* — Patrick J. Lynch
*Assistant Examiner* — Brianna T. Duckworth
(74) *Attorney, Agent, or Firm* — McAndrews, Held & Malloy, Ltd.

(57) ABSTRACT

Systems and methods are provided for welding-type headwear with enhanced movement and soft close. An example welding-type headwear has a moveable face cover configured for moving between a first position and an second position, and a movement mechanism configured for facilitating and controlling movement of the moveable face cover. The movement mechanism has a track component, a movement pin, and one or more springs. A movement assisting spring of the one or more springs is configured to assist in the moving of the moveable face cover towards to the second position. The track component has one or more tracks, and at least a portion of the movement pin is configured to move within the one or more tracks.

26 Claims, 11 Drawing Sheets

(56) References Cited

U.S. PATENT DOCUMENTS

| | | | |
|---|---|---|---|
| 2006/0064799 A1* | 3/2006 | Dion | A42B 3/326 |
| | | | 2/424 |
| 2016/0183622 A1 | 6/2016 | Patel | |
| 2021/0244125 A1 | 8/2021 | Williams | |
| 2025/0194730 A1* | 6/2025 | Kim | F16C 11/04 |

* cited by examiner

200

Moveable
Face Cover
210

Movement
Mechanism
220

Track Component 310

Damper Catch 330

Damping Spring 340

Movement Assisting Spring 350

Cam (cover) 370

Movement Pin 320

Pin Biasing Spring 360

300

First (e.g., Outer) Track 410

Tracking Structures (e.g., chamfers) 400

Second (e.g., Inner) Track 420

Damper Catch 330

Damping Spring 340

Pin Securing Structures (e.g., nobs) 440

Movement Assisting Spring 350

Channels 430

Movement Pin 320

Track Component 310

300

Movement Pin
320

First (e.g., Outer)
Track
410

Second (e.g., Inner)
Track
420

Damper Catch
330

Damping Spring
340

Track Component
310

Movement Pin
320

Track Component
310

Movement Pin
320

Cam (cover)
370

Movement Mechanism
300

First (e.g., Outer) Track 410

Damping Securing Structure 700

Damper Catch 330

Second (e.g., Inner) Track 420

Damping Spring 340

Movement Pin 320

300

Second (e.g., Inner) Track 420

First (e.g., Outer) Track 410

Movement Pin 320

Damping Securing Structure 700

Damper Catch 330

Damping Spring 340

300

800

Second (e.g., Inner) Track 420

First (e.g., Outer) Track 410

Movement Pin 320

Damper Catch 330

Damping Spring 340

300

820

WELDING-TYPE HEADWEAR WITH ENHANCED MOVEMENT AND SOFT CLOSE

CLAIM OF PRIORITY

This patent application claims priority to and claims benefit from U.S. Provisional Patent Application Ser. No. 63/619,040, filed on Jan. 9, 2024. The above identified application is hereby incorporated herein by reference in its entirety.

BACKGROUND

Welding has become increasingly ubiquitous. Welding can be performed in an automated manner or in a manual manner (e.g., being performed by a human). Various equipment or components may be used during welding operations. For example, welding helmets (or other similar welding headwear) are sometimes worn by welder (operators or users) when performing welding operations.

The welding helmets may have a hard shell configured to shield the head of an operator from welding spatter, and a viewing window so that the operator can see the surrounding environment while wearing the helmet. The viewing window may be incorporated into a moveable part.

In some instances, conventional welding solutions may have some limitations and/or disadvantages. For example, conventional welding helmets may have limitations and/or disadvantages with respect to ease of use, comfort, and the like.

Further limitations and disadvantages of conventional approaches will become apparent to one skilled in the art, through comparison of such approaches with some aspects of the present systems and methods set forth in the remainder of this disclosure with reference to the drawings.

BRIEF SUMMARY

Aspects of the present disclosure relate to welding solutions. More specifically, various implementations in accordance with the present disclosure are directed to systems and methods for welding-type headwear with enhanced movement and soft close, substantially as illustrated by or described in connection with at least one of the figures, and as set forth more completely in the claims.

These and other advantages, aspects and novel features of the present disclosure, as well as details of an illustrated implementation thereof, will be more fully understood from the following description and drawings.

DETAILED DESCRIPTION

Figure 1:
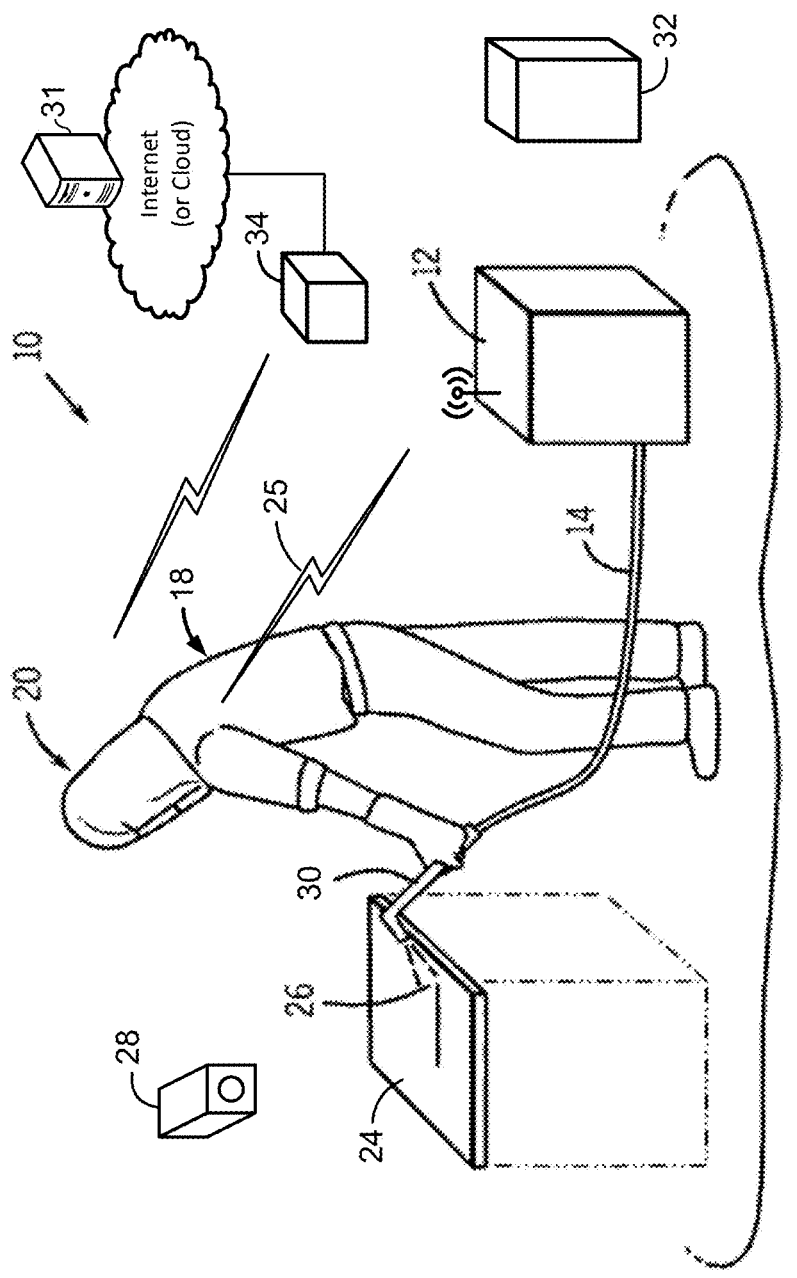
FIG. 1 shows an example welding-type setup that may be used for welding-type operations.

As utilized herein, the terms "circuits" and "circuitry" refer to physical electronic components (e.g., hardware), and any software and/or firmware ("code") that may configure the hardware, be executed by the hardware, and/or otherwise be associated with the hardware. As used herein, for example, a particular processor and memory (e.g., a volatile or non-volatile memory device, a general computer-readable medium, etc.) may comprise a first "circuit" when executing a first one or more lines of code and may comprise a second "circuit" when executing a second one or more lines of code. Additionally, a circuit may comprise analog and/or digital circuitry. Such circuitry may operate, for example, on analog and/or digital signals. It should be understood that a circuit may be in a single device or chip, on a single motherboard, in a single chassis, in a plurality of enclosures at a single geographical location, in a plurality of enclosures distributed over a plurality of geographical locations, etc. Similarly, the term "module" may, for example, refer to a physical electronic components (e.g., hardware) and any software and/or firmware ("code") that may configure the hardware, be executed by the hardware, and/or otherwise be associated with the hardware.

As utilized herein, circuitry or module is "operable" to perform a function whenever the circuitry or module comprises the necessary hardware and code (if any is necessary) to perform the function, regardless of whether performance of the function is disabled or not (e.g., by a user-configurable setting, factory trim, etc.).

As utilized herein, "and/or" means any one or more of the items in the list joined by "and/or". As an example, "x and/or y" means any element of the three-element set {(x), (y), (x, y)}. In other words, "x and/or y" means "one or both of x and y." As another example, "x, y, and/or z" means any element of the seven-element set {(x), (y), (z), (x, y), (x, z), (y, z), (x, y, z)}. In other words, "x, y and/or z" means "one or more of x, y, and z." As utilized herein, the term "exemplary" means serving as a non-limiting example, instance, or illustration. As utilized herein, the terms "for example" and "e.g." set off lists of one or more non-limiting examples, instances, or illustrations.

Welding-type power, as used herein, refers to power suitable for welding, plasma cutting, induction heating, CAC-A (carbon arc cutting/air) and/or hot wire welding/preheating (including laser welding and laser cladding). Welding-type power supply, as used herein, refers to a power supply that can provide welding-type power. A welding-type power supply may include power generation components (e.g., engines, generators, etc.) and/or power conversion circuitry to convert primary power (e.g., engine-driven power generation, mains power, etc.) to welding-type power.

Welding-type operations, as used herein, comprise operations in accordance with any known welding technique, including flame welding techniques such as oxy-fuel welding, electric welding techniques such as shielded metal arc welding (e.g., stick welding), metal inert gas welding (MIG), tungsten inert gas welding (TIG), resistance welding, as well as gouging (e.g., carbon arc gouging), cutting (e.g., plasma cutting), brazing, induction heating, soldering, and/or the like.

Welding-type setup, as used herein, refers to any setup comprising welding related devices or equipment (e.g., welding power sources, welding torch, welding gear such as headwear and the like, auxiliary devices or systems, etc.) which are used in facilitating and/or in conjunction with welding-type operations.

FIG. 1 shows an example welding-type setup that may be used for welding-type operations. Referring to FIG. 1, there is shown an example welding-type setup 10 in which an operator (user) 18 is wearing headwear 20 and welding a workpiece 24 using a torch 30 to which power is delivered by equipment 12 via a conduit 14, with weld monitoring equipment 28, which may be available for use in monitoring welding operations.

The equipment 12 may comprise a power source, optionally a source of a shield gas and, where wire/filler material is to be provided automatically, a wire feeder. Further, in some instances an engine 32 may be used to drive equipment or components used during welding operations. The engine 32 may comprise a gas engine or a liquefied petroleum (LP) engine. The engine 32 may drive generators, power sources, etc. used during welding operations.

The welding-type setup 10 of FIG. 1 may be configured to form a weld joint by any known welding-type technique. For example, optionally in any implementation, the welding equipment 12 may be arc welding equipment that provides a direct current (DC) or alternating current (AC) to a consumable or non-consumable electrode of a torch 30. The electrode delivers the current to the point of welding on the workpiece 24. In the welding-type setup 10, the operator 18 controls the location and operation of the electrode by manipulating the torch 30 and triggering the starting and stopping of the current flow. In other implementations, a robot or automated fixture may control the position of the electrode and/or may send operating parameters or trigger commands to the welding system. When current is flowing, an arc 26 is developed between the electrode and the workpiece 24. The conduit 14 and the electrode thus deliver current and voltage sufficient to create the electric arc 26 between the electrode and the workpiece. The arc 26 locally melts the workpiece 24 and welding wire or rod supplied to the weld joint (the electrode in the case of a consumable electrode or a separate wire or rod in the case of a non-consumable electrode) at the point of welding between electrode and the workpiece 24, thereby forming a weld joint when the metal cools.

Optionally in any implementation, the weld monitoring equipment 28 may be used to monitor welding operations. The weld monitoring equipment 28 may be used to monitor various aspects of welding operations, particularly in real-time (that is as welding is taking place). For example, the weld monitoring equipment 28 may be operable to monitor arc characteristics such as length, current, voltage, frequency, variation, and instability. Data obtained from the weld monitoring may be used (e.g., by the operator 18 and/or by an automated quality control system) to ensure proper welding.

As shown, the equipment 12 and headwear 20 may communicate via a link 25 via which the headwear 20 may control settings of the equipment 12 and/or the equipment 12 may provide information about its settings to the headwear 20. Although a wireless link is shown, the link may be wireless, wired, or optical.

Optionally in any implementation, equipment or components used during welding operations may be driven using engines. For example, the engine 32 may drive generators, power sources, etc. used during welding operations. In some instances, it may be desired to obtain information relating to used engines. For example, data relating to engines (and operations thereof) used during welding operations may be collected and used (e.g., based on analysis thereof) in monitoring and optimizing operations of these engines. The collection and use of such data may be performed telematically—that is, the data may be collected locally, subjected to at least some processing locally (e.g., formatting, etc.), and then may be communicated to remote management entities (e.g., centralized management locations, engine providers, etc.), using wireless technologies (e.g., cellular, satellite, etc.).

Optionally in any implementation, a dedicated controller (e.g., shown as element 34 in FIG. 1) may be used to control, centralize, and/or optimize data handling operations. The controller 34 may comprise suitable circuitry, hardware, software, or any combination thereof for use in performing various aspects of the engine related data handling operations. For example, the controller 34 may be operable to interface with the engine 32 to obtain data related thereto. The controller 34 may track or obtain welding related data (e.g., from weld monitoring equipment 28, from equipment 12, etc.). The controller 34 may then transmit the data (e.g., both engine related and weld related data), such as to facilitate remote monitoring and/or management, by way of wireless communications. This may be done using cellular and or satellite telematics hardware, for example.

In some example implementations, welding-type systems or setups, such as the welding-type setup 10, may be configured for collecting and reporting data relating to welding-type operations and/or to functions or components utilized during welding-type operations. For example, data from welding processes, power sources, welding-related accessories etc. in a weld setup may be collected. In this regard, the collected data may comprise, for example, current, voltage, wire feed speed, weld states, and numerous other power source parameters and settings.

The collected data may then be sent to remote entities (e.g., a remote server 31, which may be a manufacturer-controlled, Internet-based cloud server) and/or to local systems or devices (e.g., local PC, a tablet, a smartphone, etc.). The collected data may be utilized in enhancing welding-related systems and/or operations. For example, manufacturers may utilize the collected data to identify issues (and correct them) and/or devise modifications or improvements in the various components. Further, users may be able to generate reports on collected data to measure, document, and improve their processes.

Improving or enhancing operation of the various components of welding-type setups, such as the welding-type setup 10 of FIG. 1, is desirable. Such improvements or enhancements may be achieved by improving or enhancing particular components of welding-types setups. For example, users may wear or use welding-type headwear (e.g., the headwear 20 in FIG. 1) when performing welding-type operations in welding-type setups. Enhancing ease of use and reliability of welding-type headwear may improve performance of welding-type setups as a whole, and of welding-type operations performed therein. Such enhancements may be achieved by addressing shortcomings in existing welding-type headwear, and/or by adding features not currently available, especially where such features are added in cost effective manner. Conventional solutions may be improved upon by, e.g., enhancing features and/or functions relating to the securing of the welding-type headwear (e.g., onto the user's head).

For example, welding-type headwear (e.g., welding helmets) may incorporate a face cover that is to shield the user's face during welding operations. In this regard, as used herein, "face cover" (and/or "moveable face cover") need not be construed as having to fully cover user's face, and as such in some instances face covers (and/or moveable face covers) may cover only a part of the user's face. Such face covers may be moveable, allowing users to expose their faces, such as when not actively welding. In some instances, only the face cover may be moveable, with part of the welding-type headwear remaining fixed, secured to the user's head, thus allowing the user to move the face cover without having to remove the entire welding-type headwear. In some instances, the moveable face cover may be heavy. This may be because it has to be designed or implemented (e.g., based on selection of material used therein) to offer adequate protection, and/or because additional components may be incorporated thereto—e.g., viewing window or the like, input/output devices, circuitry, etc.

However, operating such heavy face covers may be cumbersome and/or challenging, and/or may pose health risks to the users, short- and long-term, particularly based on the manner by which face covers are moved between open (exposed) and closed (face-covered) positions. For example, it is common for users to move face covers manually, such as using their hands, by nodding their heads or the like (especially when closing the face covers), etc. Such actions may exert substantial physical strain on users, especially certain body parts thereof, such as users' necks—e.g., from constant nodding of, and needing to support relatively heavy moveable face covers, due to abrupt and relatively violent stops when the moveable face covers reach the fully closed/down positions, etc.

Solutions based on the present disclosure address some of the limitations and/or challenges that may arise with convention solutions, especially with respect to operation of face covers (or similar components) of welding-type headwear. In this regard, in various implementations, welding-type headwear may be configured such that face covers (or similar components) thereof are configured to provide enhanced closing and/or opening operations, such as by providing such features as assisted-movement, soft closing, and the like. This may be done by incorporating components to facilitate or enable such features. Example embodiments incorporating solutions and features based on the present disclosure are illustrated and described in more detail below.

Figure 2A:
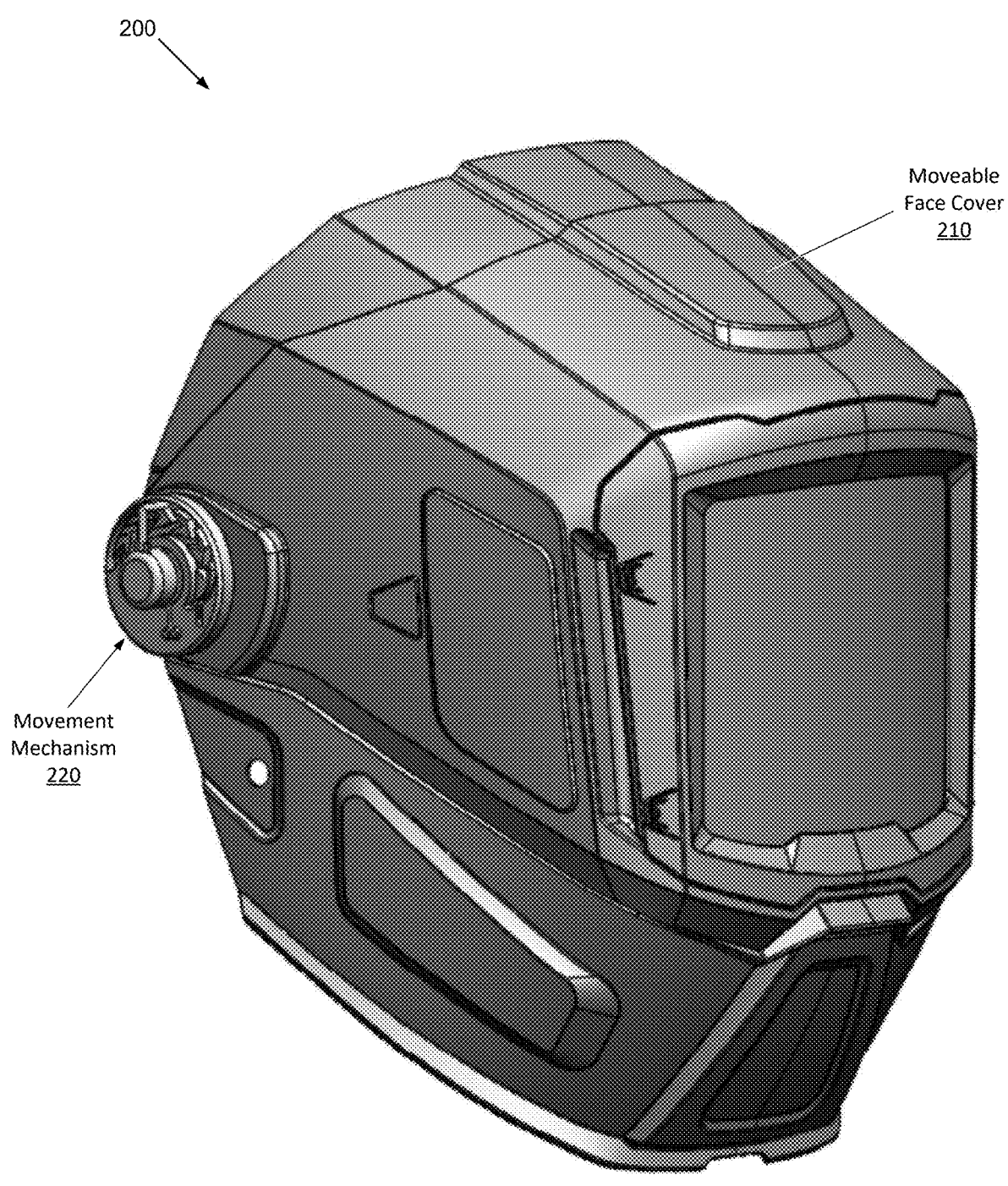
FIGS. 2A-2B show an example welding-type headwear incorporating an enhanced movement mechanism, in accordance with the present disclosure.
Figure 2B:
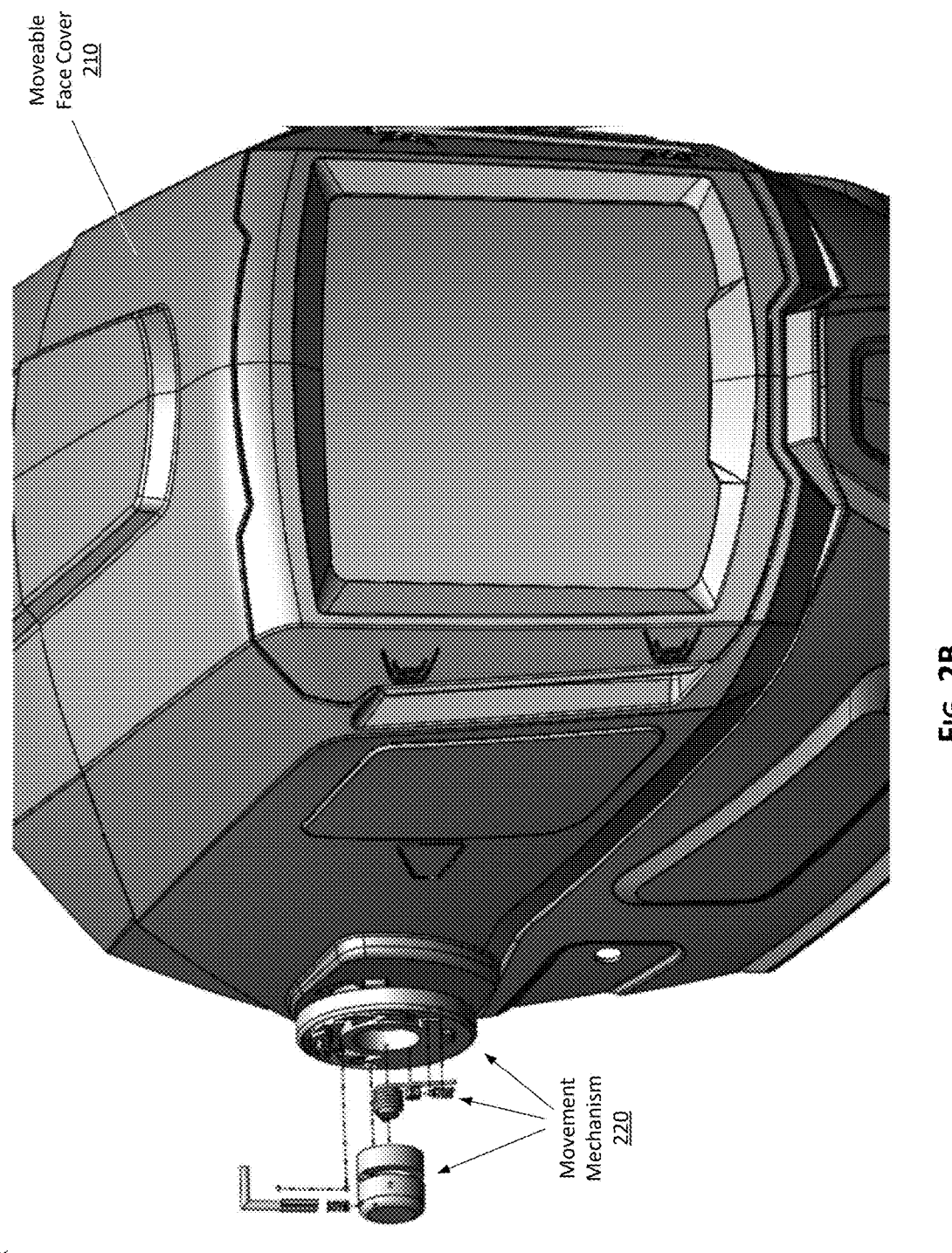

FIGS. 2A-2B show an example welding-type headwear incorporating an enhanced movement mechanism, in accordance with the present disclosure. Shown in FIGS. 2A-2B is welding-type headwear 200 (e.g., a welding helmet).

The welding-type headwear 200 may be any suitable welding-type headwear configured for use in welding-type operations. In this regard, the welding-type headwear 200 may be used (worn) by a welder (user) to provide protection thereof during the welding-type operations. The welding-type headwear 200 may be welding helmet as known in the art.

The welding-type headwear 200 may comprise a face cover 210 which may be configured to shield the face of user during welding operations. The face cover 210 may be moveable (as such it is referred to herein as "moveable face cover"), which allows the user move the moveable face cover 210 may be able to expose their faces without having to remove the entire helmet. In this regard, the moveable face cover 210 may be rotatable so that the user may raise the moveable face cover 210 away without removing the entire welding-type headwear 200. Thus, by rotating the moveable face cover 210, users may allow access to the face while keeping the shell of the welding-type headwear stationary. In some instances, the welding-type headwear 200 may also comprise a hard shell (not shown) configured to shield the head of an operator during welding operations (e.g., from welding spatter, and the like), with the moveable face cover 210 being attached to or otherwise coupled with the hard shell. Nonetheless, the disclosure is not so limited, and as such in some instances no hard shell is used, with the moveable face cover 210 being attached to, e.g., head strap or the like.

The moveable face cover 210 may incorporate a viewing window so that the user may be able look through during the welding operation. The viewing window may comprise a vision protection part, through which the user may safely look during welding-type operations. The vision protection part may comprise a darkening lens or auto-darkening filter (ADF) to protect the user's vision from the brightness of the welding arc. In some instances, welding-type headwear 200 may also include an interior face cover, which may have little or no darkening capability, and which the user may use in lower-light environments to provide protection against other conditions associated with welding-type operations—e.g., sparks, flying debris, etc. Nonetheless, it should be understood that the disclosure is not limited to any particular type or design of welding-type headwear, and solutions based on the present disclosure may apply to any welding-type headwear incorporating a moveable face cover.

In accordance with the present disclosure, welding-type headwear (such as the welding-type headwear 200) and operation thereof may be improved, particularly with respect to moveable face covers used therein, and operation thereof. In this regard, conventional welding-type headwear may have some limitations and shortcomings with respect to the operation of moveable face covers thereof. In particular, as noted above, moveable face covers may be heavy, such as due to the construction thereof (e.g., material used therein) which has to ensure adequate protection, and/or due to the additional components that may be may be incorporated thereto—e.g., viewing window or the like, input/output devices, circuitry, etc. However, operating such heavy face covers may be cumbersome and/or challenging, and/or may pose health risks to the users, short- and long-term, particularly based on the manner by which face covers are moved between open (exposed) and closed (face-covered) positions, as described above.

For example, in various conventional designs of welding-type headwear the movement (e.g., rotation) of the moveable face covers may be locked in place using locking components—e.g., two hand knobs on the outsides of the headwear. The user would have to manually tighten the moveable face covers to the user's personal preference, so the headwear's face cover stays up when needed to, and is easy enough to close, such as in response to such actions as head nodding, which cause the face cover back down before beginning or resuming welding. Such conventional solutions may cause problems as such actions (e.g., head nodding) may create ergonomic issues relating to neck strains, especially when the user is doing this for extended and/or long time. Further, the locking components (e.g., hand knobs and other plastic components) may wear over time and lead to the user needing to readjust the tightness of the headwear to keep the right tension required to perform, e.g., the head nod.

Solutions based on the present disclosure may address such issues, such as by incorporating movement mechanism that provide and/or support the various opening/closing related functions needed when operating welding-type headwear in a manner that eliminate or reduce the burden on the users. For example, in various implementations based on the present disclosure, such issues may be addressed by use of movement mechanisms that incorporate spring-assisted components (e.g., rotational spring dampers) for providing such functions as automatically closing (bring down) the face cover, soft closing at the end of the closing, multiple open positions from which the face cover may be closed, etc.

As illustrated in FIGS. 2A-2B, the welding-type headwear 200 incorporates a movement mechanism 220, which is configured based on an example embodiment of the present disclosure, to provide enhanced operation of the face cover 210, in such manner. Such mechanisms (e.g., the movement mechanism 220) may allow for enhanced operation of face coves, such as by allowing for initiating or performing certain actions, such as the closing of the face covers, in less burdensome manner. For example, to activate the face cover 210 to come down, the user may simply need to tilt their head slightly back, with spring-loaded components of the movement mechanism 220 providing the assisted movement. Once the face cover 210 comes down, suitable damping components (e.g., spring-assisted) in the movement mechanism 220 may kick in, to allow for a soft close. This will eliminate the pain points of the need for constant readjustment and neck strains. An example embodiment of movement mechanism (similar to the movement mechanism 220), and components and/or features thereof, are described in more detail below.

Figure 3:
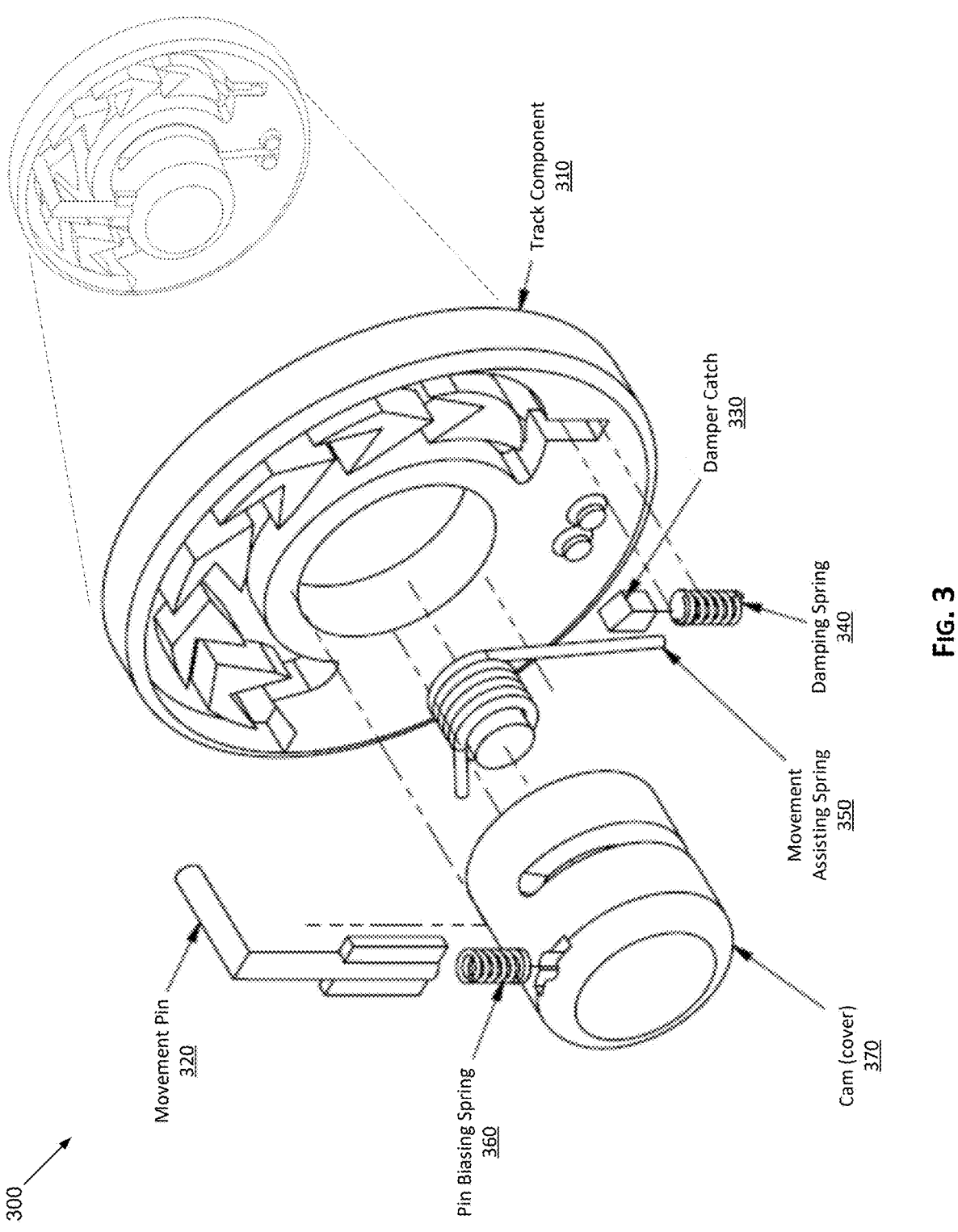
FIG. 3 shows an enhanced movement mechanism, in accordance with the present disclosure.

FIG. 3 shows an enhanced movement mechanism, in accordance with the present disclosure. Shown in FIG. 3 is movement mechanism 300, which may be used to provide assisted closing with soft close, as described herein. The movement mechanism 300 may correspond to, and may represent an example embodiment of the movement mechanism 220 of FIGS. 2A-2B.

The movement mechanism 300 may be configured for facilitating and controlling movement of a moveable face cover of a welding-type headwear (e.g., the face cover 210 of the headwear 200 of FIGS. 2A-2B) in enhanced manner. In this regard, the movement mechanism 300 may be configured for facilitating the moving of the face cover between a first position and a second position. The second position corresponds to a position of the face cover when performing welding-type operations. The second position may correspond to, e.g., a full down position, where the face fully covering the user's face while performing the welding-type operations. The first position may corresponding to any position other than the second position, which may an initial position from which the face cover is moved while it is being closed—that is, towards the second position. In some implementations, the first position may include various positions with the user's face fully or partially exposed.

The movement mechanism may comprise, at least, a track component, a movement pin, and one or more springs. For example, as illustrated in FIG. 3, the MM 300 may comprise a track component 310, a movement pin 320, a damper catch 330, a damping spring 340, a movement assisting spring 350, a pin biasing spring 360, and a cover (e.g., cam) 370.

The track component 310 may comprise a physical object that may be attached or otherwise secured to the face cover. In this regard, the tracking component 310 may comprise one or more tracks that may be traversed by the movement pin 320 during operation of the face cover. The tracking related features of track component 310 and/or functions thereof are described in more detail with respect to FIG. 4. The track component 310 may also be configured to engage at least some of the other components of the MM 300. The tracking component 310 may be a physical object, having suitable shape and/or being made from or otherwise comprising suitable material—e.g., having characteristics suitable for the design features of and/or functions attributed to the tracking component 310 as described herein may be used. As shown, the tracking component 310 may be a disc-shaped object. However, the disclosure is not limited to such shape, and any suitable shape that allow for or otherwise accommodate the design features and/or functions described herein may be used.

The movement pin 320 may comprise a physical object configured for facilitating moving of the face cover as described herein, particularly in relation to the track component 310, and specifically the tracks thereof. As shown, the movement pin 320 may comprise an L-shaped pin, having an end arranged to engage and move within the one or more tracks of the tracking component 310.

The damper catch 330 may be configured for interacting with the movement pin 320 at the end of its movement towards the second position, to provide or otherwise support the soft close as described therein, such as by means of dampening of the movement of the movement pin 320 at or near the second position.

Figure 4:
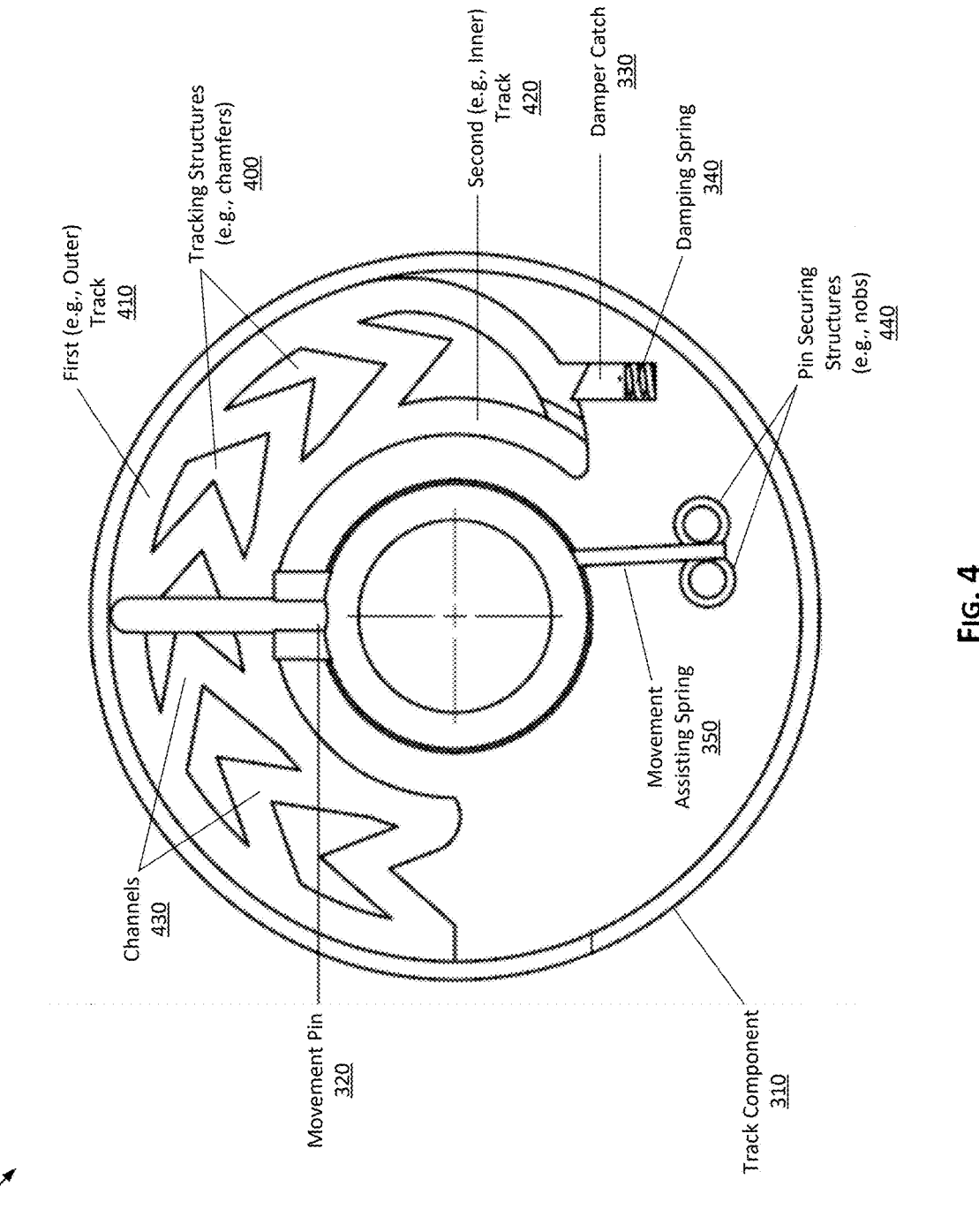
FIG. 4 shows tracking related features in an enhanced movement mechanism, in accordance with the present disclosure.

The damping spring 340 may comprise a spring configured for facilitating or otherwise supporting the dampening provided by the damper catch 330. In this regard, the damping spring 340 may be configured to dampen movement of the damper catch 330 in response to catching the movement pin 320. The damping spring 340 may comprise, e.g., a compression spring, as shown in FIG. 4.

The movement assisting spring 350 configured to assist in the moving of the face cover towards to the second position. Further, the movement assisting spring 350 may be configured to resist the moving of the moveable face cover away from the second position—that is, towards to the first position. As such, the movement pin 320 may be spring-loaded using the movement assisting spring 350, such that the movement pin 320 may be biased to constantly try to move towards to the second position. The movement assisting spring 350 may comprise, e.g., a torsion spring, as shown in FIG. 4.

The pin biasing spring 360 may be configured to bias the movement pin in particular manner. For example, in some implementations, the pin biasing spring 360 towards the edge of the tracking component 310, such that movement pin 320 is pushed into and thus travers a particular track on the tracking component 310. The pin biasing spring 360 may comprise, e.g., a compression spring, as shown in FIG. 4.

The cover 370 may comprise suitable object (e.g., cylinder-like cam or the like) configured to engage and/or cover at least some of the components of the MM 300. For example, the cover 370 may be configured to engage the movement pin 320, to house and secure in place the pin biasing spring 360, and to house and secure in place the movement assisting spring 350. In this regard, the cover 370 may be configured (e.g., based on shape and/or design thereof) to engage a section of the movement pin 320, and thus may incorporate, e.g., an opening for extending the remaining part thereof. The cover 370 may also incorporate an opening (e.g., slot-like opening) corresponding to the fixed end of the movement assisting spring 350, such that the fixed end may remain in place while the remaining art is rotating (along with the movement pin 320).

More details, and various features and/or functions of each of these components are described in more detail with respect to FIGS. 4-8C.

FIG. 4 shows tracking related features in an enhanced movement mechanism, in accordance with the present disclosure. Shown in FIG. 4 is the movement mechanism 300, illustrating in particular the track component 310 and various elements and/or features thereof.

In particular, the tracking component 310 comprises various tracks that may be traversed by the movement pin 320 during operation of a face cover (e.g., the moveable face cover 210 of FIGS. 2A-2B), and/or various physical structures that may define some of these tracks. In this regard, the tracking component 310 may be a physical object, having suitable shape and/or being made from or otherwise comprising suitable material—e.g., having characteristics suitable for the design features of and/or functions attributed to the tracking component 310 as described herein may be used. As shown, the tracking component 310 may be a disc-shaped object. However, the disclosure is not limited to such shape, and any suitable shape that allow for or otherwise accommodate the design features and/or functions described herein may be used.

The tracks may be engraved within or cut into the tracking component 310. Such engraving and/or cutting may be done based on (e.g., to create or otherwise form) the physical structures to define at least some of the tracks. For example, as illustrated in FIG. 4, the tracking component 310 comprises tracking structure(s) 400, a first (e.g., outer) track 410, a second (e.g., inner) track 420, track channel(s) 430, pin securing structures 440.

Each of the first track 410, the second track 420, and the track channel(s) 430 may be configured to accommodate the movement pin 320—e.g., having suitable dimensions (width, depth, etc.) to engage at least a portion of the movement pin 310, such that the movement pin 320 may move with these tracks/channels. For example, the tracks/channels may be engraved within or cut into the tracking component 310, and such the engraving or cutting may be done to have such suitable dimensions. Further, the movement pin 320 may be configured to ensure engaging tracking structure(s) 400, and thus moving within the first track 410, the second track 420, and the track channel(s) 430. For example, the movement pin 320 may have an L-shape ending, with one end turned downwards, into the tracking component 310, and having sufficient length such that it may extended within the recessed first track 410, second track 420, and track channel(s) 430 defined by the tracking structure(s) 400.

As shown in FIG. 4, the first track 410 may be disposed on the outside (closer to the edge of the tracking component 310 and the second track 420 track 410 may be disposed on the inside (to the inside of to the first track 410). The disclosure is not limited to such approach, however. The track channel(s) 430 may provide channels between the first track 410 and the second track 420 that the movement pin 310 (or the at least portion thereof) may traverse.

The tracking structure(s) 400 may comprise physical structures for defining or otherwise forming at least some of the first track 410, the second track 420, and the track channel(s) 430. For example, the tracking structure(s) 400 may comprise parts of the tracking component 310 that remain after the engraving or cutting thereof to form the tracks. Alternatively, the tracking structure(s) 400 may be physical structures added to the tracking component 310. The tracking structure(s) 400 may be disposed between the first track 410 and the second track 420, thus forming the track channel(s) 430 to allow movement between the two tracks. The tracking structure(s) 400 may be shaped to optimize function of the tracks as described herein. For example, in some implementations, the tracking structure(s) 400 may comprise chevron-shaped chamfers, thus giving the track channel(s) 430 corresponding chevron shapes to ensure and optimize the movement of the movement pin 320 as described herein.

The movement pin 320 may be configured such that the movement pin 310 (or the at least portion thereof) moves within the second track 420 while the movement pin 320 is being moved towards the first position, and then moves into one of the track channel(s) 430 when the moving of the movement pin 320 within the second track 420 stops. The tracking structure(s) 400 may be configured such that the movement pin 310 (or the at least portion thereof) stops within each of the track channel(s) 430 after release from second track 420. For example, the tracking structure(s) 400 may be configured such that the movement pin 310 (or the at least portion thereof) moves into the first track 410 from the tracking structure(s) 400 only in response to a releasing action. The releasing action comprise a gentle nodding or a tilting of a user's head.

The pin securing structures 440 may comprise suitable physical structures for engaging and securing the movement assisting spring 350, to ensure and/or support the use thereof in conjunction with the functions of the movement mechanism 300. For example, the pin securing structures 440 may comprise a pair of protrusion (e.g., circular in shape, as shown in FIG. 4) that extend sufficiently above the surface of the tracking component 310 and/or are spaced optimally such that they may trap an end of the movement assisting spring 350 (as shown), to keep that one stationary while the remaining part of the movement assisting spring 350 is being rotating, thus providing the requisite tensioning force for slowing the movement of the movement pin 320 within the first track 410 towards to the second position, and/or to assist in the movement of the movement pin 320 within the second track 410 away from the second position.

Figures 5A, 5B, 5C, 5D:
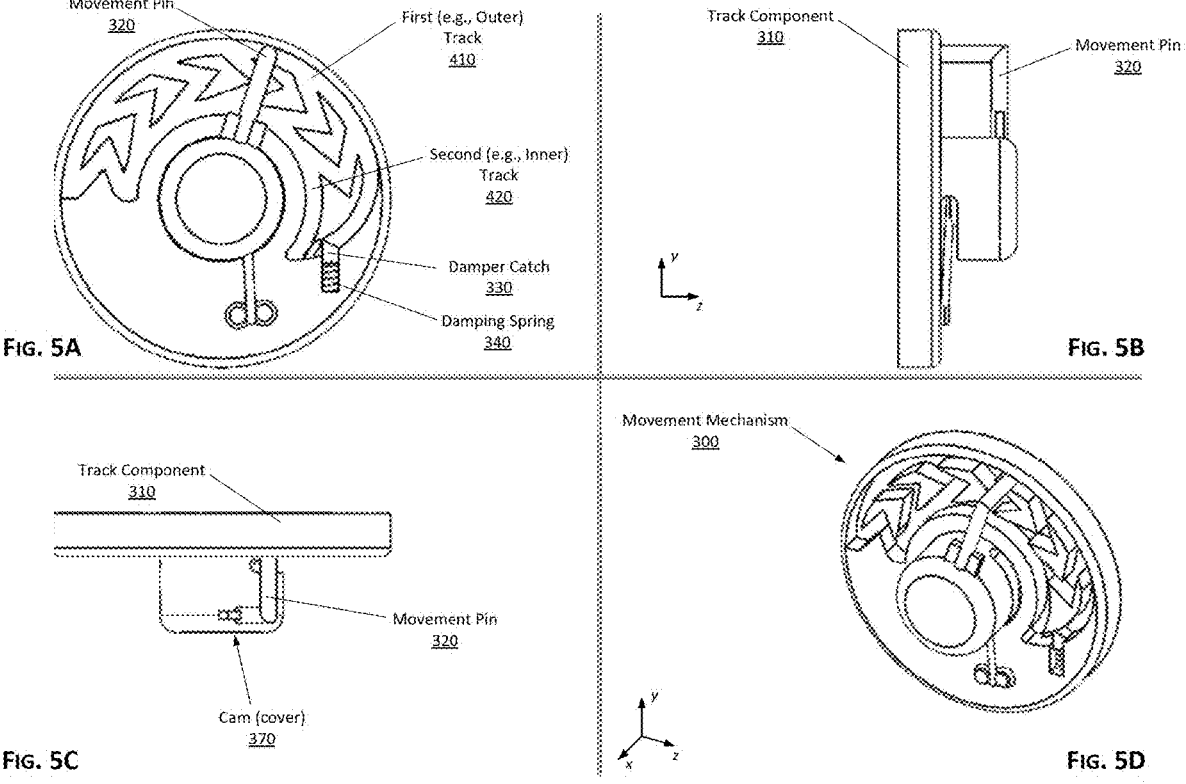
FIGS. 5A-5B show different perspectives of an enhanced movement mechanism, to illustrate example operation thereof, in accordance with the present disclosure.

FIGS. 5A-5B show different perspectives of an enhanced movement mechanism, to illustrate example operation thereof, in accordance with the present disclosure. Shown in FIGS. 5A-5B is the movement mechanism 300. In particular, shown in FIGS. 5A-5B are different perspectives of the movement mechanism 300—namely, from the side (along the z-axis as shown therein), the top (along the y-axis as shown therein), and the back (in the lateral direction, along the x-axis as shown therein), as well as a top-front-side view.

In this regard, illustrated in the FIGS. 5A-5B is one example aspect of the movement of the movement pin 320 within the track component 310 during operation of the movement mechanism 300-namely, when moving a face cover of a welding-type headwear (e.g., the face cover 210 of the welding-type headwear 200) towards the second position as described herein. In particular, as illustrated in FIGS. 5A-5B, the movement pin 320 may move within the first track 410, with the movement being associated, such as spring-loaded using the movement assisting spring 350 as described herein. As noted, the movement pin 320 moves within the first track 410 until reaching the damper catch 330, whose location corresponds to the second position. The damper catch 330 catches the movement pin 320, dampening the movement thereof (e.g., using the compression of the damping spring 340 to do), and then releases the movement pin 320 into the second track 420. The operation of the damper catch 330 and related components are illustrated in and described in more detail below with respect to FIGS. 8A-8C.

Figures 6A, 6B, 6C, 6D:
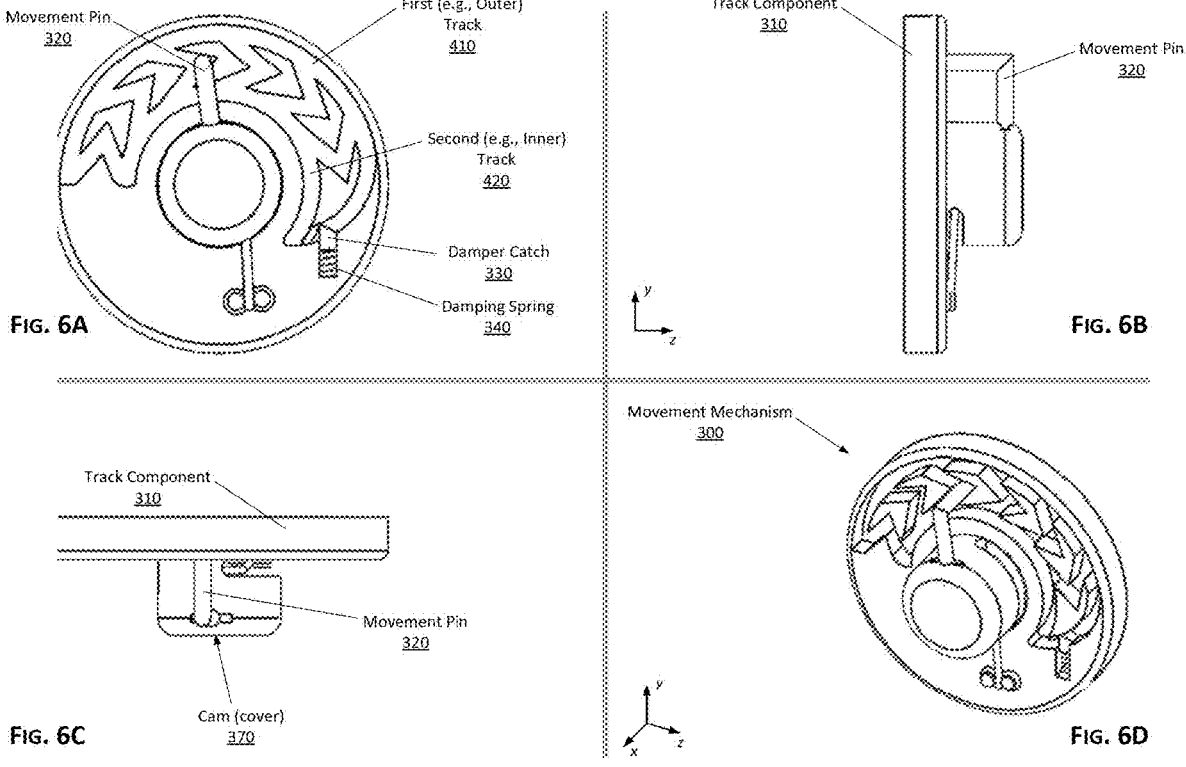
FIGS. 6A-6B show different perspectives of an enhanced movement mechanism, to illustrate example operation thereof, in accordance with the present disclosure.

FIGS. 6A-6B show different perspectives of an enhanced movement mechanism, to illustrate example operation thereof, in accordance with the present disclosure. Shown in FIGS. 6A-6B is the movement mechanism 300. In particular, shown in FIGS. 6A-6B are the same different perspectives of the movement mechanism 300 shown in FIGS. 5A-5B.

However, illustrated in the FIGS. 6A-6B is another example aspect of the movement of the movement pin 320 within the track component 310 during operation of the movement mechanism 300—namely when the movement pin 320 moves within one of the track channel(s) 430 of the track component 310. In this regard, as described herein, the movement pin 320 may be configured (e.g., biased using the pin biasing spring 360) to constantly try to move into the first track 410, and as such once moving of the movement pin 320 within the second track 420 stops, the movement pin 320 would move into the nearest track channel 430. Further, as described herein, once the movement pin 320 moves into a track channel 430, the movement pin will stop within the track channel 430 before reaching the first track 410. In this regard, as described herein, this may be achieved by configuring the track channel(s) 430 (e.g., based on the design of the tracking structure(s) 400, such as the shape thereof) such that the movement pin 320 would be trapped within each track channel 430, until a releasing action (e.g., a nodding of the head) that causes the movement pin 320 to move from the track channel 430 into the first track 410.

Figure 7:
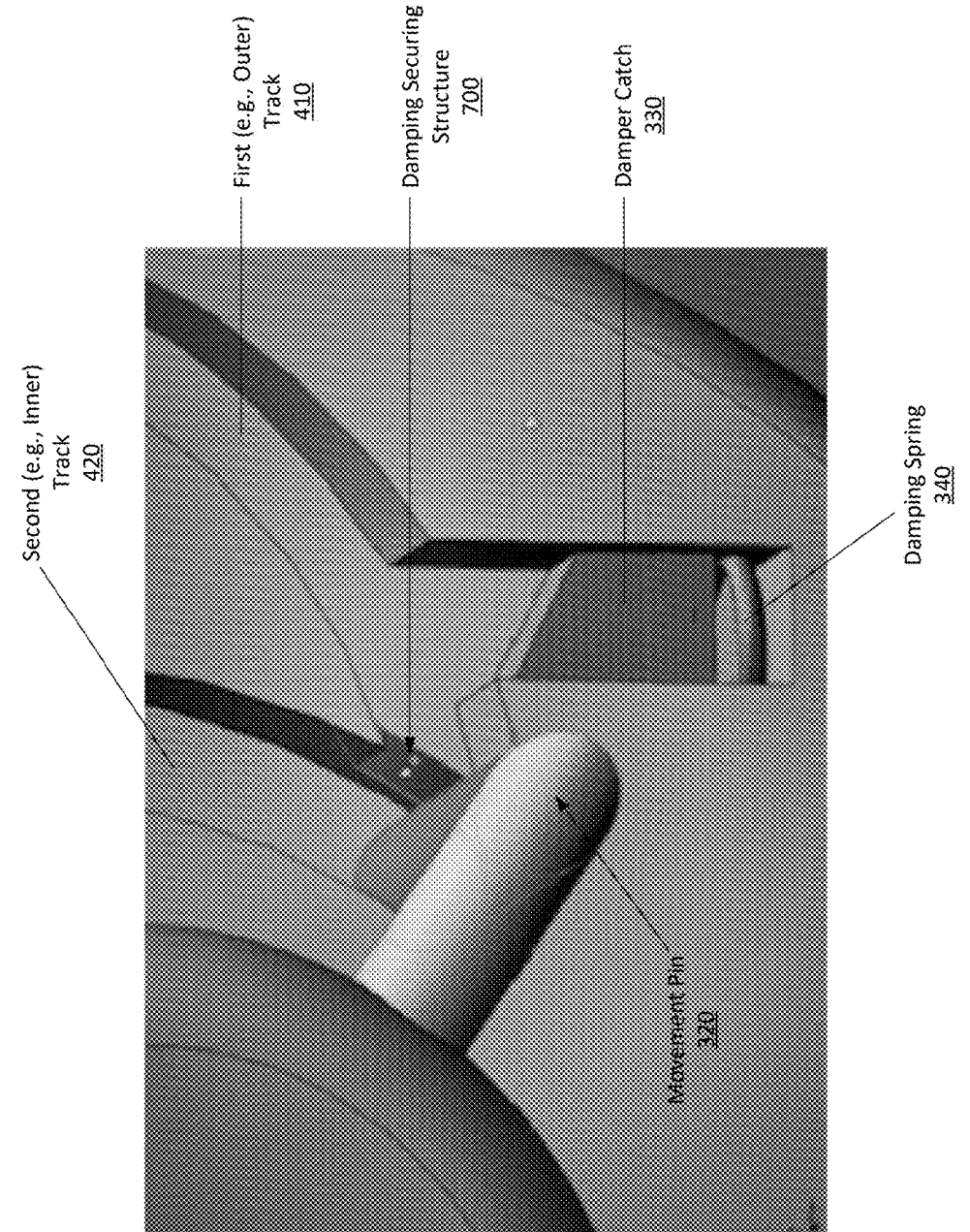
FIG. 7 shows damping related features in an enhanced movement mechanism, in accordance with the present disclosure.

FIG. 7 shows damping related features in an enhanced movement mechanism, in accordance with the present disclosure. Shown in FIG. 7 is the movement mechanism 300, and in particular a portion thereof—namely, the damper catch 330, the related components and/or features associated therewith, and the surrounding area.

In particular, shown in FIG. 7 are the damper catch 330, the damping spring 340, the movement pin 320 (or a portion thereof), and a portion of the track component 310—namely, the area corresponding to the second position, where the first track 410 and the second 420 converge.

In this regard, as described herein the damper catch 330 is configured (e.g., based on the design/shape thereof) to catch the movement pin 320 at the end of its movement within the first track 410, to facilitate the dampening of movement thereof, and to release the movement pin 320 into the second track 420. As illustrated in FIG. 7, the damper catch 330 may have a slanted top surface, configured to engage the movement pin 320 to facilitating the dampening and/or to enable the release thereof into the second track 420, and a flat bottom surface configured for engaging the damping spring 340. The dampening may be achieved by use of the damping spring 340, with the compression of the damping spring 340 resulting in slowing of the movement of the movement pin 320.

In some instances, the movement mechanism 300 may be configured to ensure that the movement pin 320 is prevented from moving back into the first track 410 (after reaching the second position). For example, the track component 310 may comprise a damping securing structure 700 that is configured (e.g., based on shape and/or physical characteristics thereof) to prevent the movement pin 300 from moving back into the first track 410 after the damper catch 330 releases the movement pin 320 into the second track 420. For example, the damping securing structure 700 may comprise a ramp, a ridge, or the like.

Figure 8A:
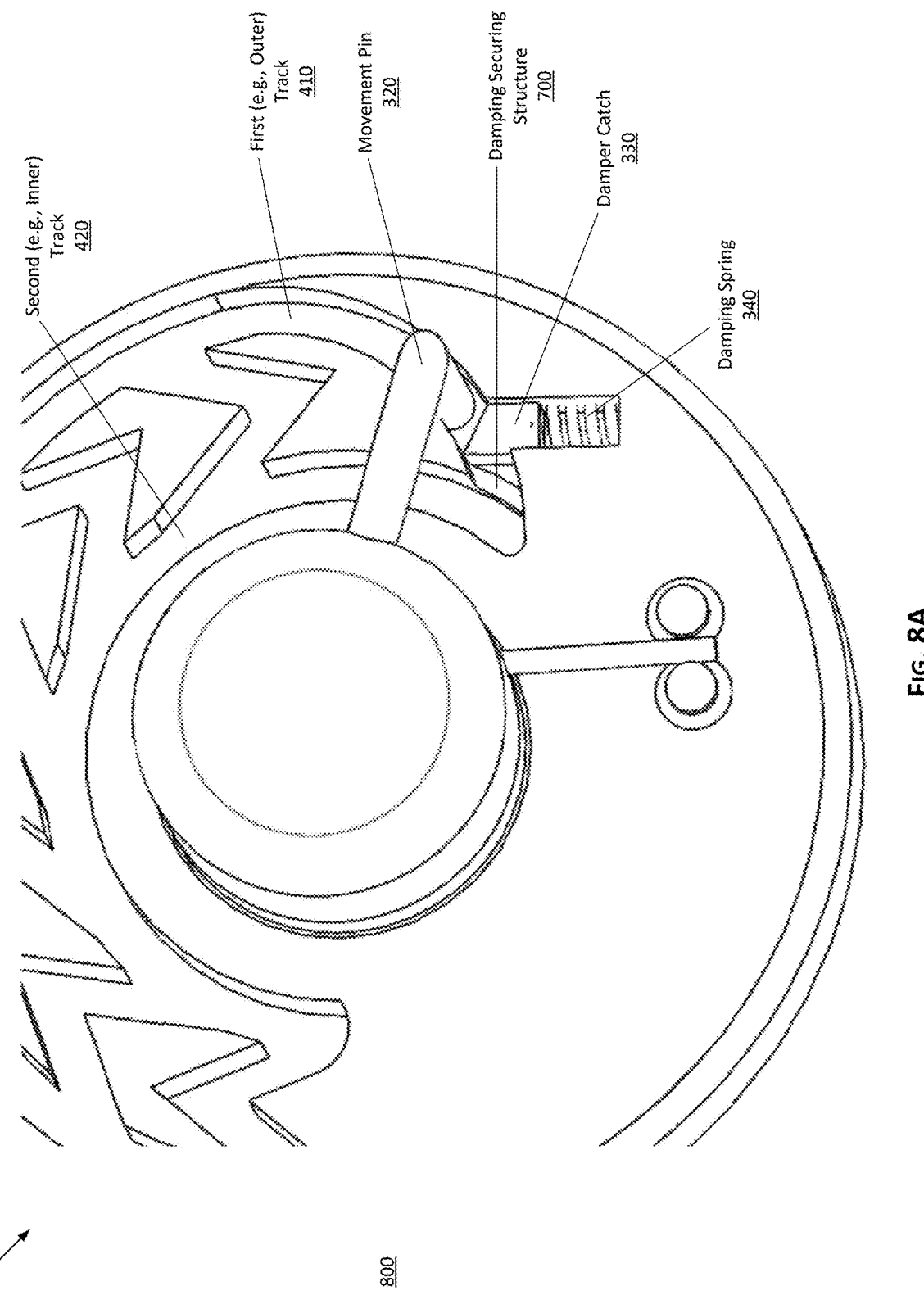
FIGS. 8A-8C show an example damping related operation in an enhanced movement mechanism, in accordance with the present disclosure.
Figure 8B:
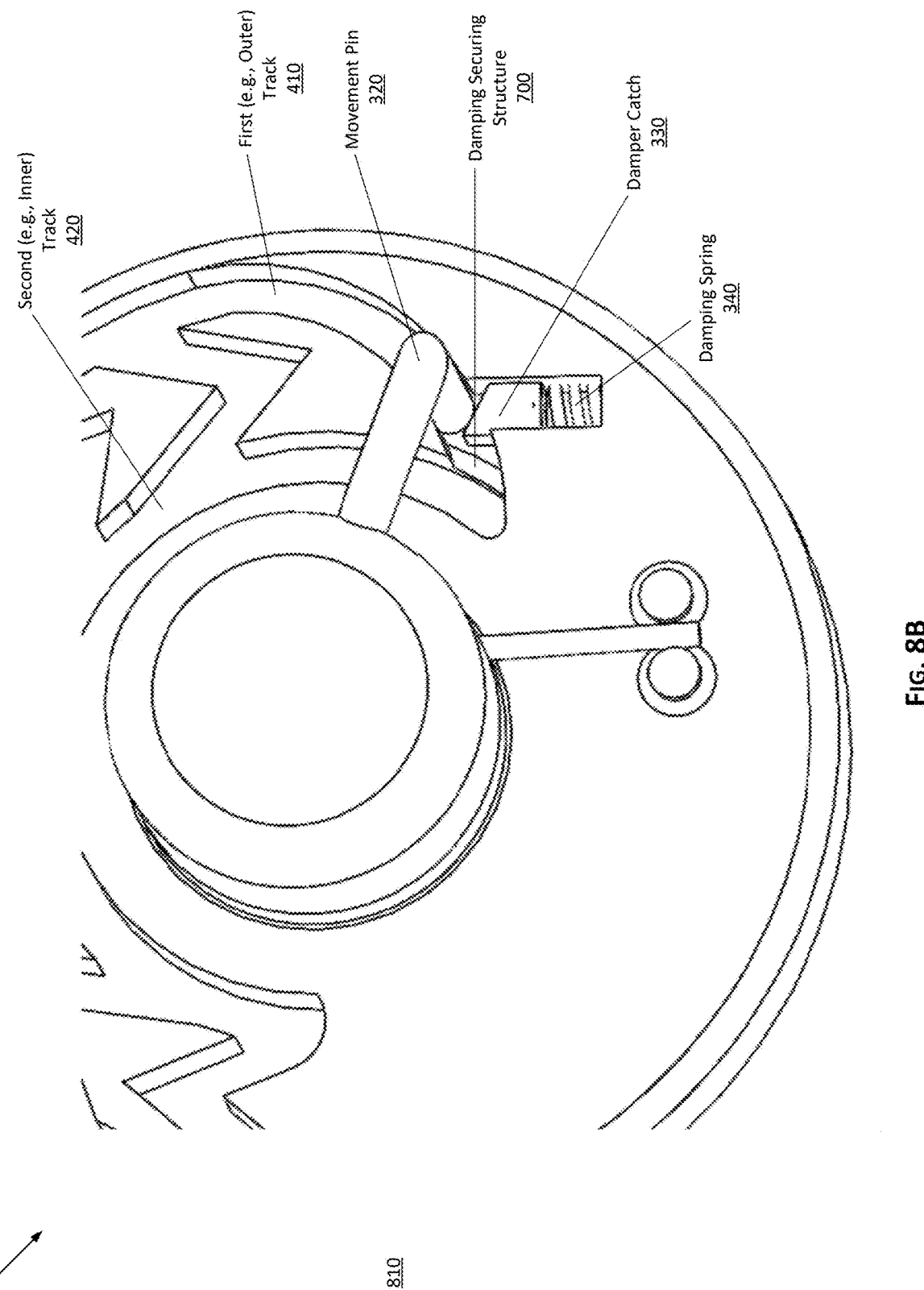
Figure 8C:
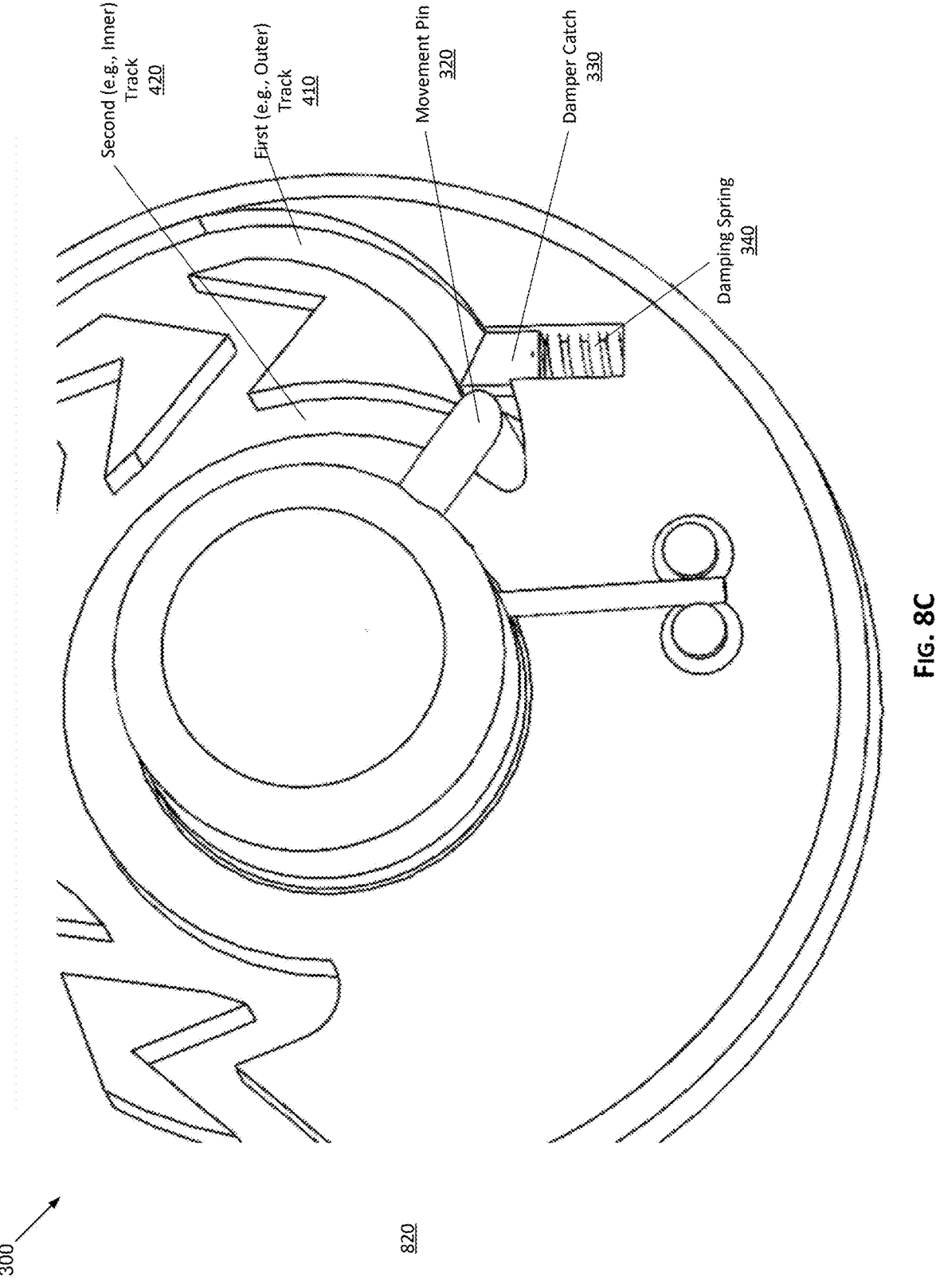

An example damping related operation utilizing the damper catch 330, and the related components and/or features associated therewith, is illustrated and described in more detail with respect to FIGS. 8A-8C.

FIGS. 8A-8C show an example damping related operation in an enhanced movement mechanism, in accordance with the present disclosure. Shown in FIGS. 8A-8C is the movement mechanism 300, and in particular a portion thereof—namely, the damper catch 330 and the surrounding area.

In particular, shown in FIGS. 8A-8C are the damper catch 330, the damping spring 340, the damping securing structure 700, the movement pin 320 (or a portion thereof), and a portion of the track component 310—namely, the area corresponding to the second position, where the first track 410 and the second 420 converge. Illustrated in FIGS. 8A-8C is sequence of events that may occur during example damping related operation in the movement mechanism 300.

In particular, during a first stage 800 of the operation, illustrated in FIG. 8A, the movement pin 320 is moving within the first track 410, and approaching the second position, and thus approaching the damper catch 330, whose location corresponds to the second position. In this regard, as explained herein, the movement of the movement pin 320 is assisted—e.g., spring-loaded, with the tensioning of the movement assisting spring 350 providing the required spring-loading.

During a second stage 810 of the operation, illustrated in FIG. 8B, the movement pin 320 reaches the damper catch 330. In this regard, as described herein, the damper catch 330 is configured to catch the movement pin 320 and to dampen the movement thereof, such as by pressing on the damping spring 340, in response to the movement pin 320 pushing on damper catch 330, with the compression of the damping spring 340 slowing the movement of the movement pin 320. The damper catch 330 may block the movement pin 320 from moving any further, during the dampening thereof. In this regard, the slanted top surface of the damper catch 330 may facilitate (and optimize) the engaging of the movement pin 320 when it reaches and presses against the damper catch 330 during the dampening phase, and the blocking of the movement pin 320. Further, flat bottom surface of the damper catch 330 is configured to engage the damping spring 340 and press against, in response to the pressing against the damper catch 330 by the movement pin 320, causing the compressing of the damping spring 340, and thus dampening of the movement pin 320.

During a third stage 820 of the operation, illustrated in FIG. 8C, the dampening of the movement pin 320 is completed, and the movement pin 320 is released into the second track 420. In this regard, as described herein, the damper catch 330 is configured to facilitate the releasing of the movement pin 320 into the second track 420. This may be done by use of the slanted top surface. In this regard, as the movement pin 320 contacts and presses against the slanted top surface during the dampening phase, it remains trapped within the first track 410, until the damper catch 330 compresses the damping spring 340 enough that the slanted top surface clears sufficient space between the first track 410 and the second track 420, allowing the movement pin 320 to move into the second track 420. Once the movement pin 320 to moves into the second track 420, the pressure on the damper catch 330 is relieved, allowing the damper catch 330 to reset. In this regard, the resetting of the damper catch 330 may occur as a result of the damping spring 340 decompressing, causing the damper catch 330 to move up—that is, move back into its initial/disengaged position (as shown in FIG. 8A). To that end, the damping securing structure 700 may guard against the movement pin 320 moving back into the first track 410, before the resetting of the damper catch 330 is complete.

Accordingly, solutions based on the present disclosure may yield various advantages over any existing conventional solutions. In this regard, with the features and functions incorporated into the welding-type headwear based on the present disclosure, the welding-type headwear may stay on the user's head on with sufficient tightness, and may provide new users and regular users a way to know exactly how much to tighten their welding-type headwear. This may be done while also accommodating more experienced users, by offering adjustability of the tightness pre-set values so that such experienced users may set customized tightness. Further, auto-release features may allow for quick-release, and thus removal of the welding-type headwear, if desired.

An example welding-type system, in accordance with the present disclosure, comprises a welding-type headwear configured for use during welding-type operations, the welding-type headwear comprising a moveable face cover configured for moving between a first position and an second position; and a movement mechanism configured for facilitating and controlling movement of the moveable face cover, wherein the movement mechanism comprises a track component, a movement pin, and one or more springs; and wherein a movement assisting spring of the one or more springs is configured to assist in the moving of the moveable face cover towards to the second position; the track component comprises one or more tracks; and at least a portion of the movement pin is configured to move within the one or more tracks.

In an example embodiment, the second position corresponds to a position where the moveable face cover fully covers a face of a user of the welding-type headwear.

In an example embodiment, the movement assisting spring of the one or more springs is configured to resist the moving of the moveable face cover towards to the first position.

In an example embodiment, the movement assisting spring of the one or more springs comprises a torsion spring.

In an example embodiment, the movement pin is spring-loaded using the movement assisting spring of the one or more springs such that it is biased to constantly try to move towards to the second position.

In an example embodiment, the movement mechanism further comprises a damper catch configured to catch and dampen movement of the movement pin when the moveable face cover reaches the second position.

In an example embodiment, a damping spring of the one or more springs is configured to dampen movement of the damper catch in response to catching the movement pin.

In an example embodiment, the damping spring of the one or more springs comprises a compression spring.

In an example embodiment, the track component comprises a first track and a second track, and wherein the movement pin is configured to move towards to the second position using the first track.

In an example embodiment, a pin biasing spring of the one or more springs is configured to bias the movement pin into the first track.

In an example embodiment, the movement mechanism further comprises a damper catch configured to catch the movement pin when the moveable face cover reaches the second position and to release the movement pin into the second track.

In an example embodiment, the damper catch is configured to release the movement pin into the second track when the damper catch clears a track channel that allows pin to move through between the first track and the second track. In this regard, clearing enough space for the movement point to pass through occurs when the compression spring is sufficiently (or fully) compressed.

In an example embodiment, the track component comprises a damping securing structure configured to prevent the movement pin from moving back into the first track after the damper catch releases the movement pin into the second track.

In an example embodiment, the damping securing structure comprises a ramp or a ridge.

In an example embodiment, the first track is an outer track and the second track is an inner track.

In an example embodiment, the track component further comprises a plurality of physical tracking structures forming a plurality of track channels between the first track and the second track.

In an example embodiment, the at least portion of the movement pin is configured to move within the first track, the second track, and the plurality of track channels.

In an example embodiment, the plurality of physical tracking structures is disposed between the first track and the second track.

In an example embodiment, the movement pin is configured to engage each of the plurality of physical tracking structures.

In an example embodiment, the movement pin is configured such that the at least portion of the movement pin moves within the second track while the movement pin is being moved towards the first position, and the at least portion of the movement pin moves into one of the plurality of track channels when the moving of the movement pin within the second track stops.

In an example embodiment, the plurality of physical tracking structures is configured such that the at least portion of the movement pin stops within each of the plurality of track channels after release from second track.

In an example embodiment, the plurality of physical tracking structures is configured such that the at least portion of the movement pin moves into the first track from the plurality of physical tracking structures only in response to a releasing action.

In an example embodiment, the releasing action comprise a nodding or a tilting of a user's head.

In an example embodiment, the plurality of physical tracking structures comprises a plurality of chevron-shaped chamfers.

In an example embodiment, the track component comprises a disc-shaped object.

In an example embodiment, the one or more tracks are engraved within or cut into the track component.

In an example embodiment, the welding-type headwear comprises a welding helmet.

Other implementations in accordance with the present disclosure may provide a non-transitory computer readable medium and/or storage medium, and/or a non-transitory machine readable medium and/or storage medium, having stored thereon, a machine code and/or a computer program having at least one code section executable by a machine and/or a computer, thereby causing the machine and/or computer to perform the processes as described herein.

Accordingly, various implementations in accordance with the present disclosure may be realized in hardware, software, or a combination of hardware and software. The present disclosure may be realized in a centralized fashion in at least one computing system, or in a distributed fashion where different elements are spread across several interconnected computing systems. Any kind of computing system or other apparatus adapted for carrying out the methods described herein is suited. A typical combination of hardware and software may be a general-purpose computing system with a program or other code that, when being loaded and executed, controls the computing system such that it carries out the methods described herein. Another typical implementation may comprise an application specific integrated circuit or chip.

Various implementations in accordance with the present disclosure may also be embedded in a computer program product, which comprises all the features enabling the implementation of the methods described herein, and which when loaded in a computer system is able to carry out these methods. Computer program in the present context means any expression, in any language, code or notation, of a set of instructions intended to cause a system having an information processing capability to perform a particular function either directly or after either or both of the following: a) conversion to another language, code or notation; b) reproduction in a different material form.

While the present disclosure has been described with reference to certain implementations, it will be understood by those skilled in the art that various changes may be made and equivalents may be substituted without departing from the scope of the present disclosure. For example, block and/or components of disclosed examples may be combined, divided, re-arranged, and/or otherwise modified. In addition, many modifications may be made to adapt a particular situation or material to the teachings of the present disclosure without departing from its scope. Therefore, it is intended that the present disclosure not be limited to the particular implementation disclosed, but that the present disclosure will include all implementations falling within the scope of the appended claims.

What is claimed is:

1. A welding system, comprising:
a welding headwear configured for use during welding operations, the welding headwear comprising:
a moveable face cover configured for moving between a first position and an second position; and
a movement mechanism configured for facilitating and controlling movement of the moveable face cover, wherein the movement mechanism comprises a track component, a movement pin, and one or more springs; and
wherein:
a movement assisting spring of the one or more springs is configured to assist in the moving of the moveable face cover towards to the second position;
the track component comprises one or more tracks; and
at least a portion of the movement pin is configured to move within the one or more tracks; and
wherein the movement pin is spring-loaded using the movement assisting spring of the one or more springs such that the movement pin is biased to constantly try to move towards to the second position.

2. The welding system according to claim 1, wherein the second position corresponds to a position where the moveable face cover fully covers a face of a user of the welding headwear.

3. The welding system according to claim 1, wherein the movement assisting spring of the one or more springs is configured to resist the moving of the moveable face cover towards to the first position.

4. The welding system according to claim 1, wherein the movement assisting spring of the one or more springs comprises a torsion spring.

5. The welding system according to claim 1, wherein the movement mechanism further comprises a damper catch configured to catch and dampen movement of the movement pin when the moveable face cover reaches the second position.

6. The welding system according to claim 5, wherein a damping spring of the one or more springs is configured to dampen movement of the damper catch in response to catching the movement pin.

7. The welding system according to claim 6, wherein the damping spring of the one or more springs comprises a compression spring.

8. The welding system according to claim 1, wherein the track component comprises a first track and a second track, and wherein the movement pin is configured to move towards to the second position using the first track.

9. The welding system according to claim 8, wherein the first track is an outer track and the second track is an inner track.

10. The welding system according to claim 8, wherein the track component further comprises a plurality of physical tracking structures forming a plurality of track channels between the first track and the second track.

11. The welding system according to claim 10, wherein the plurality of physical tracking structures is disposed between the first track and the second track.

12. The welding system according to claim 1, wherein the track component comprises a disc-shaped object.

13. The welding system according to claim 1, wherein the one or more tracks are engraved within or cut into the track component.

14. The welding system according to claim 1, wherein the welding headwear comprises a welding helmet.

15. A welding system, comprising:
a welding headwear configured for use during welding operations, the welding headwear comprising:
a moveable face cover configured for moving between a first position and an second position; and
a movement mechanism configured for facilitating and controlling movement of the moveable face cover, wherein the movement mechanism comprises a track component, a movement pin, and one or more springs; and
wherein:
a movement assisting spring of the one or more springs is configured to assist in the moving of the moveable face cover towards to the second position;
the track component comprises one or more tracks; and
at least a portion of the movement pin is configured to move within the one or more tracks;
wherein the track component comprises a first track and a second track, and wherein the movement pin is configured to move towards to the second position using the first track; and
wherein a pin biasing spring of the one or more springs is configured to bias the movement pin into the first track.

16. A welding system, comprising:
a welding headwear configured for use during welding operations, the welding headwear comprising:
   a moveable face cover configured for moving between a first position and an second position; and
   a movement mechanism configured for facilitating and controlling movement of the moveable face cover, wherein the movement mechanism comprises a track component, a movement pin, and one or more springs; and
   wherein:
      a movement assisting spring of the one or more springs is configured to assist in the moving of the moveable face cover towards to the second position;
      the track component comprises one or more tracks; and
      at least a portion of the movement pin is configured to move within the one or more tracks;
      wherein the track component comprises a first track and a second track, and wherein the movement pin is configured to move towards to the second position using the first track; and
      wherein the movement mechanism further comprises a damper catch configured to catch the movement pin when the moveable face cover reaches the second position and to release the movement pin into the second track.

17. The welding system according to claim 16, wherein the damper catch is configured to release the movement pin into the second track when the damper catch clears a track channel that allows pin to move through between the first track and the second track.

18. The welding system according to claim 16, wherein the track component comprises a damping securing structure configured to prevent the movement pin from moving back into the first track after the damper catch releases the movement pin into the second track.

19. The welding system according to claim 18, wherein the damping securing structure comprises a ramp or a ridge.

20. A welding system, comprising:
a welding headwear configured for use during welding operations, the welding headwear comprising:
   a moveable face cover configured for moving between a first position and an second position; and
   a movement mechanism configured for facilitating and controlling movement of the moveable face cover, wherein the movement mechanism comprises a track component, a movement pin, and one or more springs; and
   wherein:
      a movement assisting spring of the one or more springs is configured to assist in the moving of the moveable face cover towards to the second position;
      the track component comprises one or more tracks; and
      at least a portion of the movement pin is configured to move within the one or more tracks;
      wherein the track component comprises a first track and a second track, and wherein the movement pin is configured to move towards to the second position using the first track;
      wherein the track component further comprises a plurality of physical tracking structures forming a plurality of track channels between the first track and the second track; and wherein the at least portion of the movement pin is configured to move within the first track, the second track, and the plurality of track channels.

21. A welding system, comprising:
a welding headwear configured for use during welding operations, the welding headwear comprising:
   a moveable face cover configured for moving between a first position and an second position; and
   a movement mechanism configured for facilitating and controlling movement of the moveable face cover, wherein the movement mechanism comprises a track component, a movement pin, and one or more springs; and
   wherein:
      a movement assisting spring of the one or more springs is configured to assist in the moving of the moveable face cover towards to the second position;
      the track component comprises one or more tracks; and
      at least a portion of the movement pin is configured to move within the one or more tracks;
      wherein the track component comprises a first track and a second track, and wherein the movement pin is configured to move towards to the second position using the first track;
      wherein the track component further comprises a plurality of physical tracking structures forming a plurality of track channels between the first track and the second track; and
      wherein the movement pin is configured to engage each of the plurality of physical tracking structures.

22. A welding system, comprising:
a welding headwear configured for use during welding operations, the welding headwear comprising:
   a moveable face cover configured for moving between a first position and an second position; and
   a movement mechanism configured for facilitating and controlling movement of the moveable face cover, wherein the movement mechanism comprises a track component, a movement pin, and one or more springs; and
   wherein:
      a movement assisting spring of the one or more springs is configured to assist in the moving of the moveable face cover towards to the second position;
      the track component comprises one or more tracks; and
      at least a portion of the movement pin is configured to move within the one or more tracks;
      wherein the track component comprises a first track and a second track, and wherein the movement pin is configured to move towards to the second position using the first track;
      wherein the track component further comprises a plurality of physical tracking structures forming a plurality of track channels between the first track and the second track; and
      wherein the movement pin is configured such that the at least portion of the movement pin moves within the second track while the movement pin is being moved towards the first position, and the at least portion of the movement pin moves into one of the plurality of track channels when the moving of the movement pin within the second track stops.

23. The welding system according to claim 22, wherein the plurality of physical tracking structures is configured such that the at least portion of the movement pin stops within each of the plurality of track channels after release from second track.

24. The welding system according to claim 23, wherein the plurality of physical tracking structures is configured such that the at least portion of the movement pin moves into the first track from the plurality of physical tracking structures only in response to a releasing action.

25. The welding system according to claim 24, wherein the releasing action comprise a nodding or a tilting of a user's head.

26. A welding system, comprising:

a welding headwear configured for use during welding operations, the welding headwear comprising:

a moveable face cover configured for moving between a first position and an second position; and a movement mechanism configured for facilitating and controlling movement of the moveable face cover, wherein the movement mechanism comprises a track component, a movement pin, and one or more springs; and wherein:

a movement assisting spring of the one or more springs is configured to assist in the moving of the moveable face cover towards to the second position;

the track component comprises one or more tracks; and at least a portion of the movement pin is configured to move within the one or more tracks;

wherein the track component comprises a first track and a second track, and wherein the movement pin is configured to move towards to the second position using the first track;

wherein the track component further comprises a plurality of physical tracking structures forming a plurality of track channels between the first track and the second track; and wherein the plurality of physical tracking structures comprises a plurality of chevron-shaped chamfers.

* * * * *